US00PP18968P2

(12) United States Plant Patent
Kramer

(10) Patent No.: US PP18,968 P2
(45) Date of Patent: Jun. 24, 2008

(54) ***GERANIUM* PLANT NAMED 'RAINBOW'**

(50) Latin Name: *Geranium wallichianum*
Varietal Denomination: Rainbow

(75) Inventor: Hans Kramer, Ede (NL)

(73) Assignee: Compass Plants B.V., Hillegom (NL)

( * ) Notice: Subject to any disclaimer, the term of this patent is extended or adjusted under 35 U.S.C. 154(b) by 0 days.

(21) Appl. No.: 11/705,865

(22) Filed: Feb. 14, 2007

(51) Int. Cl.
*A01H 5/00* (2006.01)

(52) U.S. Cl. ..... Plt./324

(58) Field of Classification Search ..... Plt./324
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Geranium* plant named 'Rainbow', characterized by its upright and broadly outwardly spreading plant habit; basal branching growth habit; freely flowering habit; purple violet, purple and light purple tri-colored flowers with dark purple-colored venation; and good garden performance.

2 Drawing Sheets

Botanical designation: *Geranium wallichianum.*
Cultivar denomination: 'Rainbow'.

BACKGROUND OF THE INVENTION

The present invention relates to a new and distinct cultivar of *Geranium,* botanically known as *Geranium wallichianum,* and hereinafter referred to by the name 'Rainbow'.

The new *Geranium* originated from a cross-pollination of two unnamed selections of *Geranium wallichianum,* not patented. The new *Geranium* was discovered and selected by the Inventor as a single flowering plant from within the progeny of the stated cross-pollination grown in a controlled environment in Ede, The Netherlands in July, 2002.

Asexual reproduction of the new *Geranium* by terminal cuttings in a controlled environment in Zandvoort, The Netherlands since January, 2004, has shown that the unique features of this new *Geranium* are stable and reproduced true to type in successive generations.

SUMMARY OF THE INVENTION

The cultivar Rainbow has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Rainbow'. These characteristics in combination distinguish 'Rainbow' as a new and distinct cultivar of *Geranium:*

1. Upright and broadly outwardly spreading plant habit.
2. Basal branching growth habit.
3. Freely flowering habit.
4. Purple violet, purple and light purple tri-colored flowers with dark purple-colored venation.
5. Good garden performance.

Plants of the new *Geranium* differ primarily from plants of the parent selections in flower color as plants of the parent selections have pink-colored flowers.

Plants of the new *Geranium* can be compared to plants of the *Geranium* cultivar Buxton Blue, not patented. In side-by-side comparisons conducted in The Netherlands, plants of the new *Geranium* differed primarily from plants of the cultivar Buxton Blue in flower color as plants of the cultivar Buxton Blue had blue and white-colored flowers. In addition, plants of the new *Geranium* are more compact than plants of the cultivar Buxton Blue.

BRIEF DESCRIPTION OF THE PHOTOGRAPHS

The accompanying colored photographs illustrate the overall appearance of the new *Geranium,* showing the colors as true as it is reasonably possible to obtain in colored reproductions of this type. Colors in the photographs may differ slightly from the color values cited in the detailed botanical description which accurately describe the colors of the new *Geranium.*

The photograph at the top of the first sheet comprises a side perspective view of a typical flowering plant of 'Rainbow' grown in a container.

The photograph at the bottom of the first sheet is a close-up view of a typical leaf of 'Rainbow'.

The photograph on the second sheet is a close-up view of a typical flower of 'Rainbow'.

DETAILED BOTANICAL DESCRIPTION

The aforementioned photographs and following observations, measurements and values describe plants grown in Ede, The Netherlands in an outdoor nursery during the summer and autumn. During the production of the plants, day temperatures ranged from 12° C. to 26° C. and night temperatures ranged from 4° C. to 14° C. Plants were about one year old when the photographs and the description were taken. In the detailed description, color references are made to The Royal Horticultural Society Colour Chart, 2001 Edition, except where general terms of ordinary dictionary significance are used.

Botanical classification: *Geranium wallichianum* cultivar Rainbow.

Parentage:

*Female, or seed, parent.*—Unnamed selection of *Geranium wallichianum,* not patented.

*Male, or pollen, parent.*—Unnamed selection of *Geranium wallichianum,* not patented.

Propagation:

*Type.*—By terminal cuttings.

*Time to initiate roots.*—About three weeks at temperatures of 20° C.

*Time to produce a rooted young plant.*—About six weeks at temperatures of 20° C.

*Root description.*—Fine, fibrous; white in color.

*Rooting habit.*—Freely branching, moderately dense.

Plant description:

*General appearance.*—Upright and broadly outwardly spreading plant habit.

*Growth and branching habit.*—Moderately vigorous growth habit. Basal branching habit with about three lateral branches per plant.

*Plant height.*—About 16 cm.

*Plant width.*—About 47 cm.

*Lateral branches.*—Length: About 12.9 cm. Diameter: About 2 mm. Internode length: About 7.1 cm. Texture: Pubescent. Strength: Moderately strong. Color: 143B.

Foliage description:

*Arrangement.*—Opposite; simple.

*Length.*—About 6.9 cm.

*Width.*—About 7.9 cm.

*Shape.*—Orbicular to roughly reniform; palmately lobed.

*Apex.*—Acute.

*Base.*—Hastate.

*Margin.*—Palmately lobed; lobes bi-serrate.

*Venation pattern.*—Palmate.

*Texture, upper and lower surfaces.*—Densely pubescent.

*Color.*—Developing foliage, upper surface: Darker than between 141A and 143A. Developing foliage, lower surface: 138B. Fully developed, upper surface: 137A; venation, 137A. Fully developed, lower surface: Between 137C and 138A; venation, 138B.

*Petiole.*—Length: About 6.9 cm. Diameter: About 1.5 mm. Texture, upper and lower surfaces: Pubescent. Color, upper and lower surfaces: 144A.

Flower description:

*Flower arrangement.*—Single rotate flowers arranged in pairs arising from apical leaf axils. Flowers face upright or outward. Flowers not persistent. Flowers not fragrant.

*Quantity of flowers.*—Freely flowering habit; about twelve flower buds and open flowers per lateral branch.

*Flowering season.*—In The Netherlands, flowering is continuous from early May into October.

*Flower longevity.*—Flowers last about one week on the plant.

*Flower diameter.*—About 4.2 cm.

*Flower depth (height).*—About 1.2 cm.

*Flower buds.*—Length: About 8 mm. Diameter: About 3 mm. Shape: Elliptic. Color: 143A.

*Petals.*—Quantity per flower: Five in a single whorl. Length: About 2.3 cm. Width: About 1.7 cm. Shape: Obcordate. Apex: Retuse. Base: Attenuate. Margin: Entire. Texture, upper and lower surfaces: Mostly smooth; towards the base, densely pubescent. Color: When opening and fully opened, upper surface: Towards the margins, N82B; mid-section and random splashes towards the margins, close to N78B; towards the base, close to 77C to 77D; venation, N79C. Color becoming closer to N87A to N87B with development. When opening and fully opened, lower surface: Close to N81C to N81D; venation, N78A.

*Sepals.*—Quantity per flower: Five, arranged in a single whorl. Length: About 1.3 cm. Width: About 4 mm. Shape: Ovate. Apex: Aristate. Base: Cuneate. Margin: Entire. Texture, upper and lower surfaces: Sparsely pubescent. Color: When opening, upper surface: Between 143B and 144A. When opening, lower surface: 143A to 143B. Fully opened, upper and lower surfaces: 143B.

*Peduncles.*—Length: About 9.1 cm. Diameter: About 1 mm. Strength: Strong. Angle: About 10° from vertical. Texture: Pubescent. Color: 146B to 146C.

*Pedicels.*—Length: About 4.5 cm. Diameter: About 1 mm. Strength: Moderately strong. Angle: About 40° from vertical. Texture: Pubescent. Color: 144B.

*Reproductive organs.*—Androecium: Stamen quantity per flower: About ten. Filament length: About 9 mm. Filament color: N186D. Anther length: About 2.5 mm. Anther shape: Oblong. Anther color: Between N186A to 202A. Pollen amount: Scarce. Pollen color: 196D. Gynoecium: Pistil quantity per flower: One. Pistil length: About 7 mm. Stigma shape: Five-parted; reflexed. Stigma color: N186C. Style length: About 3 mm. Style color: 60A. Ovary color: 143A to 143B.

*Fruits.*—Length: About 4.3 cm. Diameter: About 1.4 cm. Color: Towards the base, N170B; towards the apex, N199A to N199B.

*Seeds.*—Quantity per fruit: About five. Length: About 4 mm. Diameter: About 2 mm. Color: 200A.

Disease/pest resistance: Plants of the new *Geranium* have not been observed to be resistant to pathogens and pests common to *Geraniums.*

Garden performance: Plants of the new *Geranium* have exhibited good tolerance to rain and wind and have been observed to tolerate temperatures ranging from about −15° C. to about 35° C.

It is claimed:

1. A new and distinct *Geranium* plant named 'Rainbow' as illustrated and described.

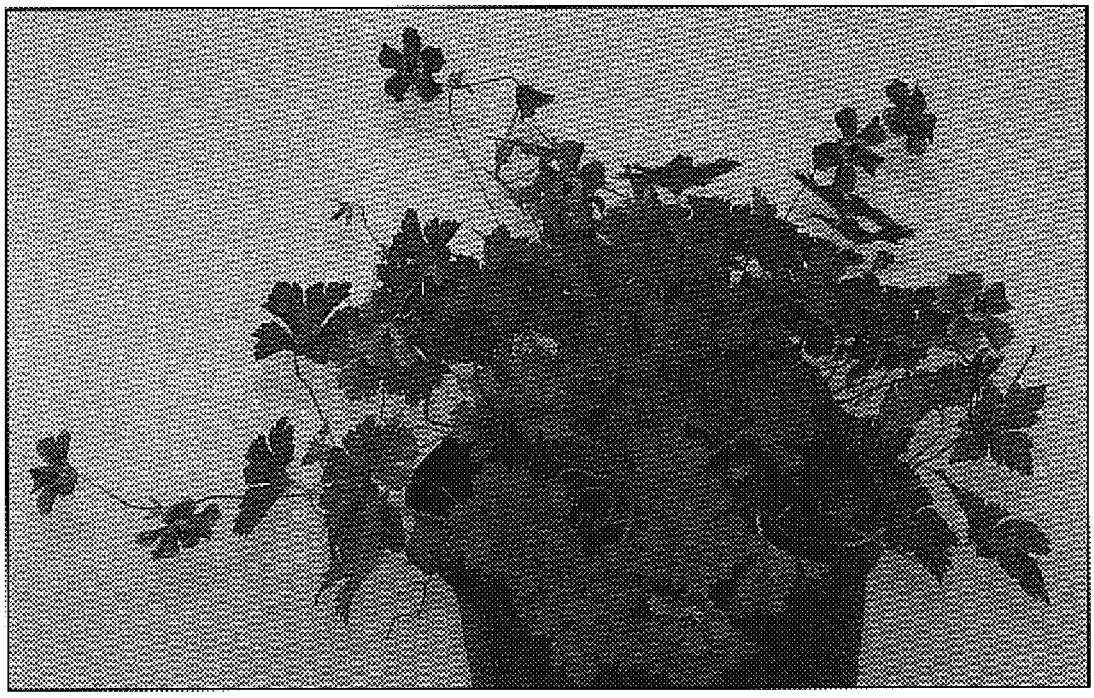
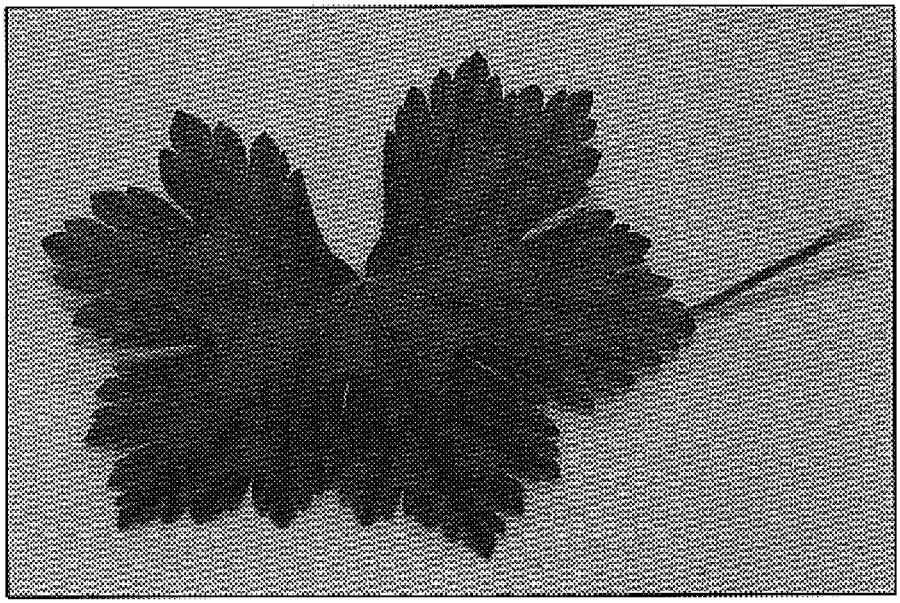

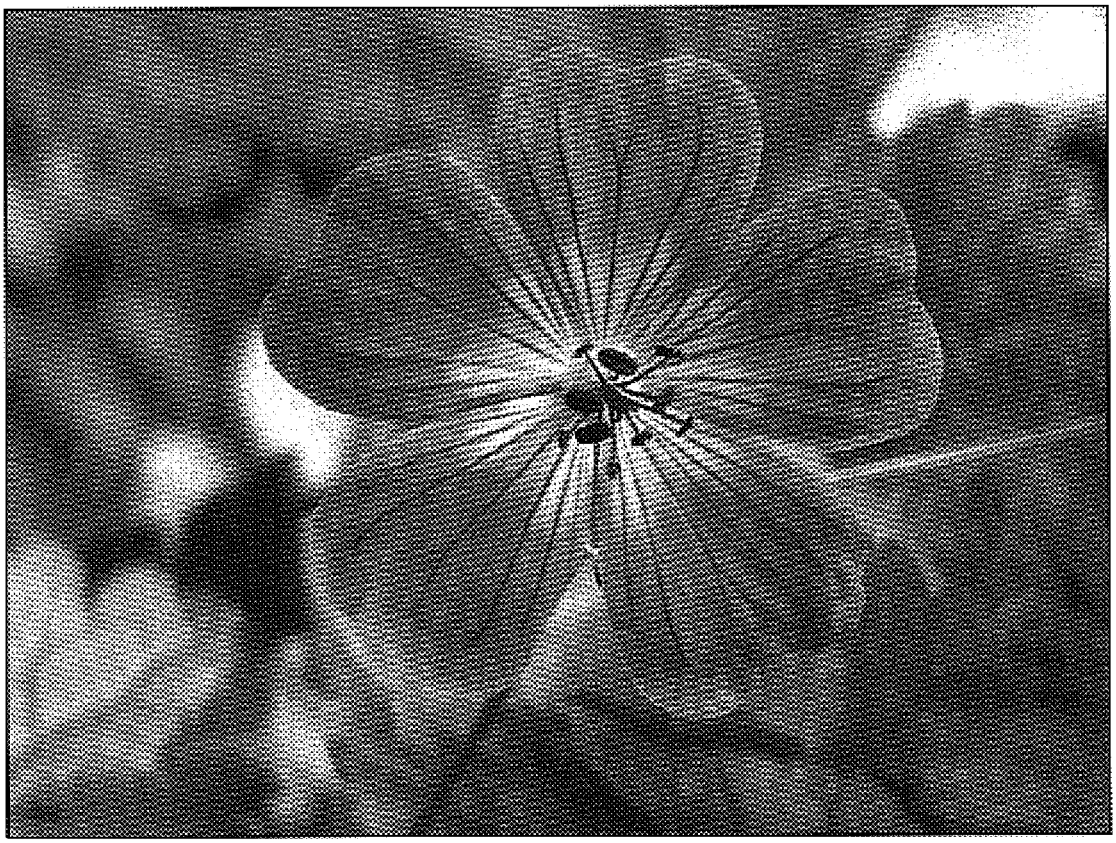

* * * * *